United States Patent [19]

Zaleski, II

[11] Patent Number: 5,588,815
[45] Date of Patent: Dec. 31, 1996

[54] SURGICAL CASSETTE LOADING AND UNLOADING SYSTEM

[75] Inventor: Richard L. Zaleski, II, San Juan Capistrano, Calif.

[73] Assignee: Alcon Laboratories, Inc., Fort Worth, Tex.

[21] Appl. No.: 559,016

[22] Filed: Nov. 15, 1995

[51] Int. Cl.⁶ .................................................. F04B 43/08
[52] U.S. Cl. .................. 417/477.2; 604/153; 128/DiG. 12
[58] Field of Search .................. 417/476, 477.1, 417/477.2, 477.3; 604/151, 153, 154; 128/DIG. 12

[56] References Cited

U.S. PATENT DOCUMENTS

| | | |
|---|---|---|
| 3,756,752 | 9/1973 | Stenner .................................. 417/477 |
| 4,256,442 | 3/1981 | Lamadrid et al. ...................... 417/477 |
| 4,493,695 | 1/1985 | Cook . |
| 4,626,248 | 12/1986 | Scheller . |
| 4,627,833 | 12/1986 | Cook . |
| 4,713,051 | 12/1987 | Steppe et al. . |
| 4,758,220 | 7/1988 | Sundblom et al. . |
| 4,758,238 | 7/1988 | Sundblom et al. . |
| 4,790,816 | 12/1988 | Sundblom et al. . |
| 4,798,580 | 1/1989 | DeMeo et al. . |
| 5,125,891 | 6/1992 | Hossain et al. . |
| 5,230,614 | 7/1993 | Zanger et al. . |
| 5,267,956 | 12/1993 | Beuchat . |
| 5,364,342 | 11/1994 | Beuchat et al. . |
| 5,387,088 | 2/1995 | Knapp et al. . |

FOREIGN PATENT DOCUMENTS 973924  11/1982  U.S.S.R. ............................ 417/477.1

*Primary Examiner*—Charles G. Freay
*Attorney, Agent, or Firm*—Jeffrey S. Schira

[57] ABSTRACT

A surgical cassette unloading and unloading system having a peristaltic pump roller head with a flared and beveled notch and a plunger or probe that engages the cassette peristaltic pump tube.

2 Claims, 5 Drawing Sheets

SURGICAL CASSETTE LOADING AND UNLOADING SYSTEM

BACKGROUND OF THE INVENTION

The present invention relates to surgical cassettes and more particularly to a system for loading and unloading surgical cassettes.

The use of cassettes with surgical instruments to help manage irrigation and aspiration flows into a surgical site are well-known. U.S. Pat. Nos. 4,493,695, 4,627,833 (Cook), U.S. Pat. No. 4,395,258 (Wang, et al.), U.S. Pat. No. 4,713,051 (Steppe, et al.), U.S. Pat. No. 4,798,850 (DeMeo, et al.), U.S. Pat. Nos. 4,758,238, 4,790,816 (Sundblom, et al.) and U.S. Pat. No. 5,267,956, 5,364,342 (Beuchat) all disclose tubeless or tube-type surgical cassettes and are incorporated herein in their entirety by reference.

One of the primary function of the cassettes disclosed above is to control aspiration (vacuum) level at the surgical site. The vacuum generating device generally is contained within the surgical system control console and may be a venturi, diaphragm or peristaltic pump. When a peristaltic pump is used, the cassette generally contains a peristaltic pump tube that may be compressed within a race by a rotating pump roller head (e.g. U.S. Pat. No. 4,713,051, Steppe, et al.) or may be stretched over the rotating pump roller head (e.g. U.S. Pat. Nos. 5,267,956 and 5,364,342, Beuchat). When the pump tube is stretched over the roller head, it may be difficult not only to install the pump tube over the roller head, but also to remove the pump tube from the roller head. The operation of peristaltic pump roller heads, and particularly peristaltic pump roller heads used in ophthalmic instruments, is more fully disclosed in U.S. Pat. No. 5,230,614 (Zanger, et al.), and U.S. Pat. No. 5,387,088 (Knapp, et al.), the contents of which are incorporated herein by reference.

Accordingly, a need exists for a system to assist in loading and unloading a surgical cassette.

BRIEF DESCRIPTION OF THE INVENTION

The present invention includes a peristaltic pump roller head with a flared and beveled notch in combination with a plunger or probe that engages the cassette peristaltic pump tube. When the cassette is installed in the console, the roller head is rotated so that the flared notch of the roller head engages the tube and pulls the tube over the roller head. When the cassette is removed from the console, the roller head is counter-rotated while the plunger telescopes to push the pump tube away from the roller head. The counter-rotation of the roller head together with the bevel on the roller head and the action of the plunger disengages the pump tube from the roller head.

Accordingly, one objective of the present invention is to provide a system for simplifying the loading and unloading of surgical cassettes.

Another objective of the present invention is to provide a system for loading a peristaltic pump tube onto a peristaltic pump roller head.

Still another objective of the present invention is to provide a system for unloading a peristaltic pump tube from a peristaltic pump roller head.

These and other objectives and advantages of the present invention will become apparent from the detailed description and claims which follow.

DETAILED DESCRIPTION OF THE INVENTION

Figure 1:
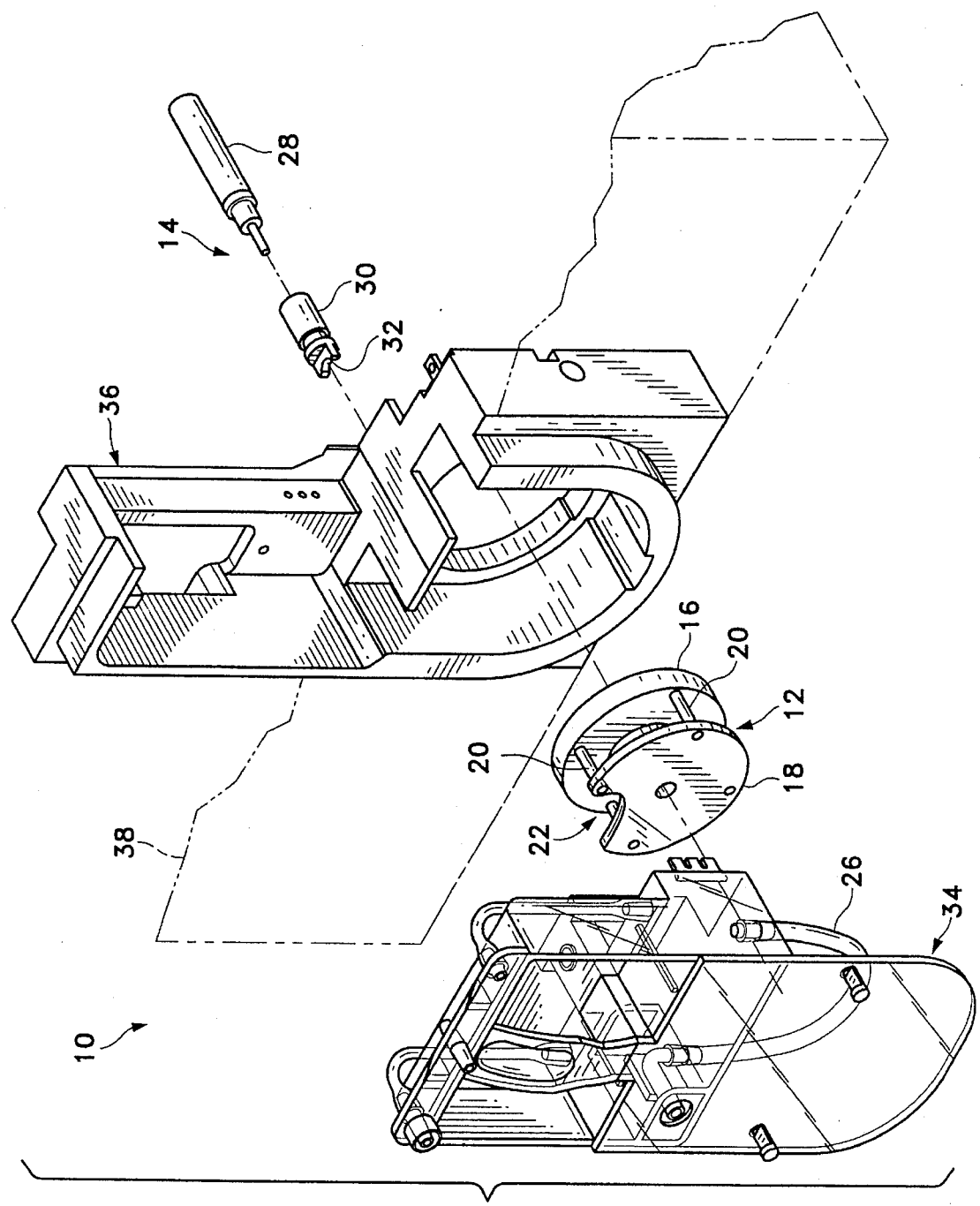
FIG. 1 is an exploded perspective view of the present invention.
Figure 2:
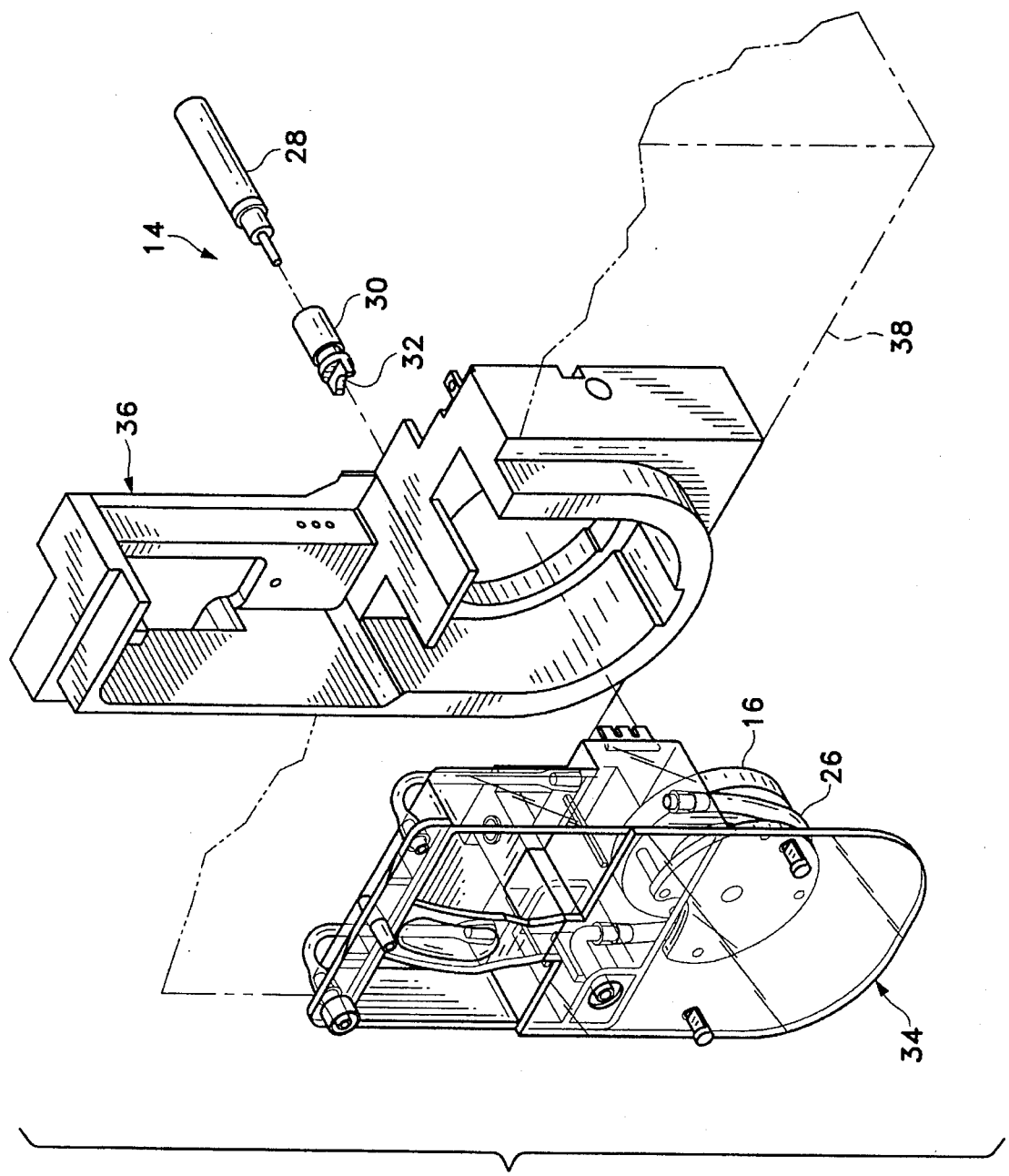
FIG. 2 is an exploded perspective view of the present invention, similar to FIG. 1 but depicting the peristaltic pump tube engaged on the peristaltic pump roller head.
Figure 4:
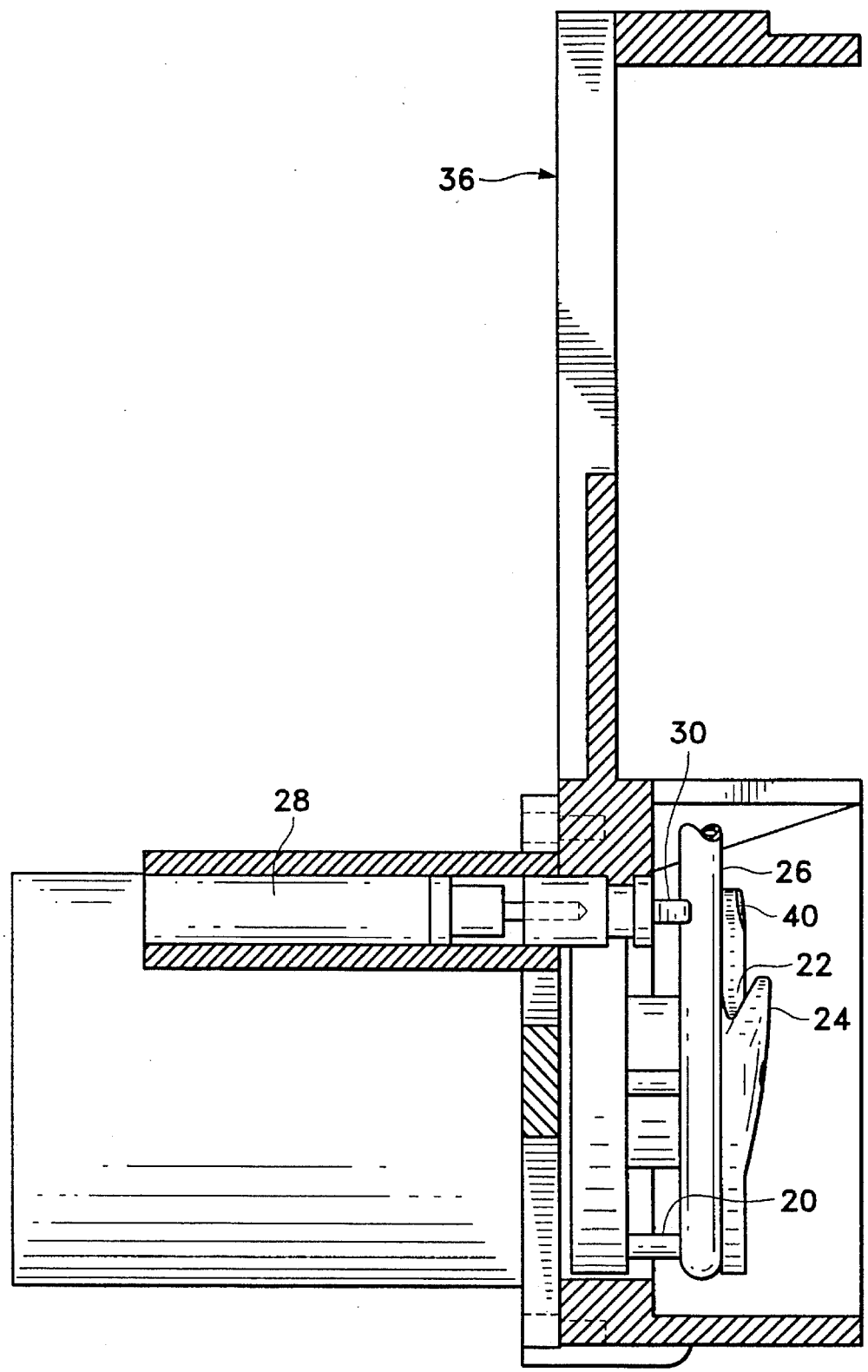
FIG. 4 is a cross-sectional view of the present invention taken along line 4—4 in FIG. 3.

As best seen in FIGS. 1 and 2, system 10 of the present invention generally consists of roller head 12 and plunger assembly 14. Roller head 12 generally consists of inner plate 16 and outer plate 18 joined by a plurality of rollers 20. Outer plate 18 contains notch 22 and, as best seen in FIG. 4, outer plate 18 has flared portion 24 and beveled portion 40, both bordering notch 22. Notch 22, flared portion 24 and beveled portion 40 operate to assist in the loading and unloading of peristaltic pump tube 26 in the manner described below.

Figure 5:
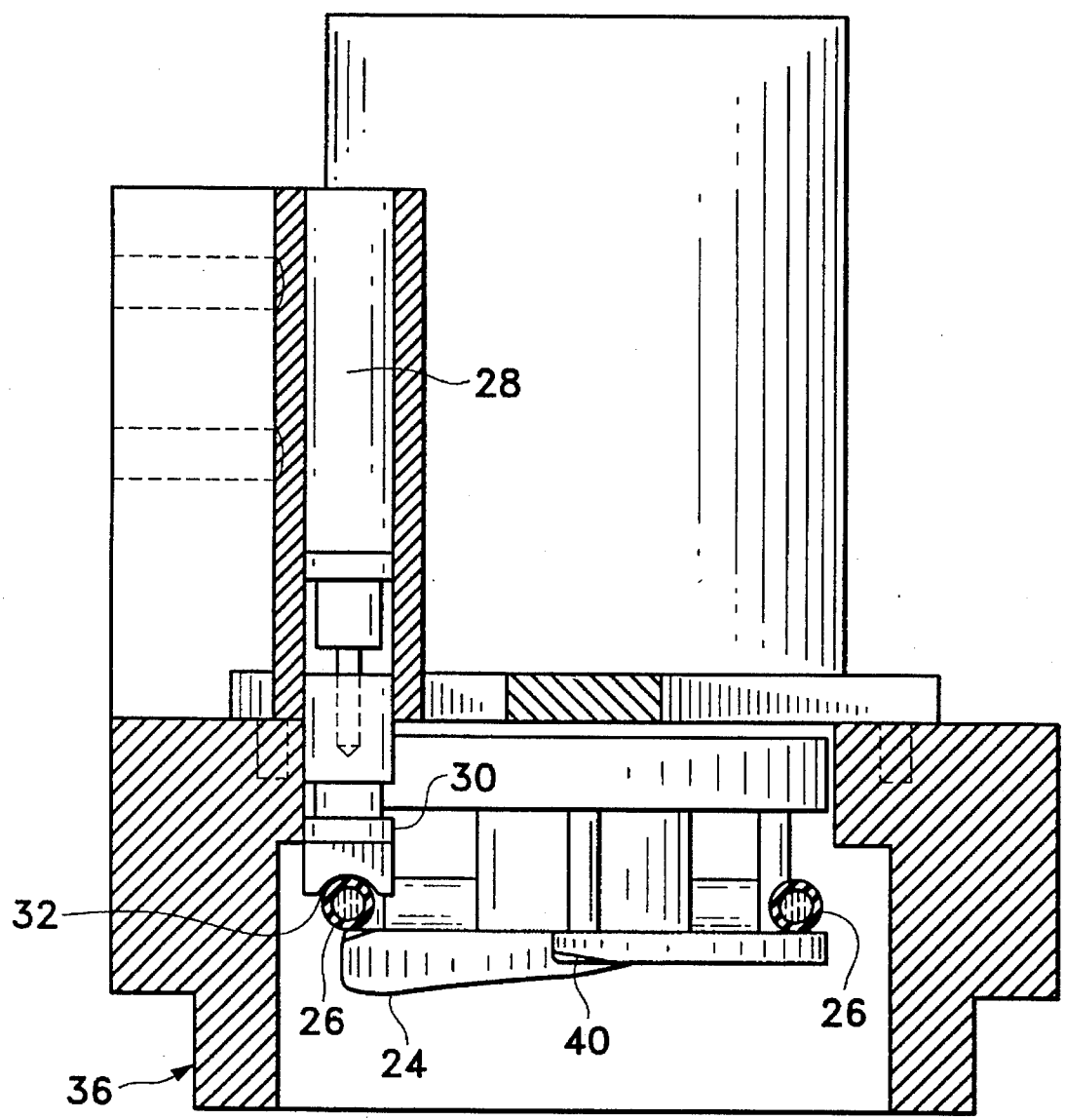
FIG. 5 is a cross-sectional view of the present invention taken along line 5—5 in FIG. 3.

Plunger assembly 14 generally consists of cylinder 28 and tip 30. Cylinder 28 may be any of a variety of electrically or hydraulically extendable cylinders, but a pneumatic cylinder with a power generation range of between 4.0 pound-feet and 5.0 pound-feet, and an extension range of between 0 inches and 0.4 inches is preferred. Suitable cylinders 28 are commercially available from sources such as American Cylinder Company, Inc. Tip 30 preferably is approximately 1 inch long and made from aluminum or an aluminum alloy. As can be seen in FIGS. 1, 2 and 5, tip 30 contains an arcuate cutout 32 of approximately the same radius as pump tube 26 (e.g., 0.125 inches) so that tip 30 engages pump tube 26 without slipping off.

In use, cassette 34 containing pump tube 26 is installed within cassette receiving portion 36 of surgical console 38 so that pump tube 26 is pressed against outer plate 18 of roller head 12. In order to provide peristaltic pumping action, pump tube 26 must be stretched over rollers 20 contained in roller head 12. To assist is this process, flared portion 24 of outer plate 18 projects out from outer plate 18. As roller head 12 is rotated, flared portion 24 engages pump tube 26, thereby threading pump tube 26 over rollers 20.

Figure 3:
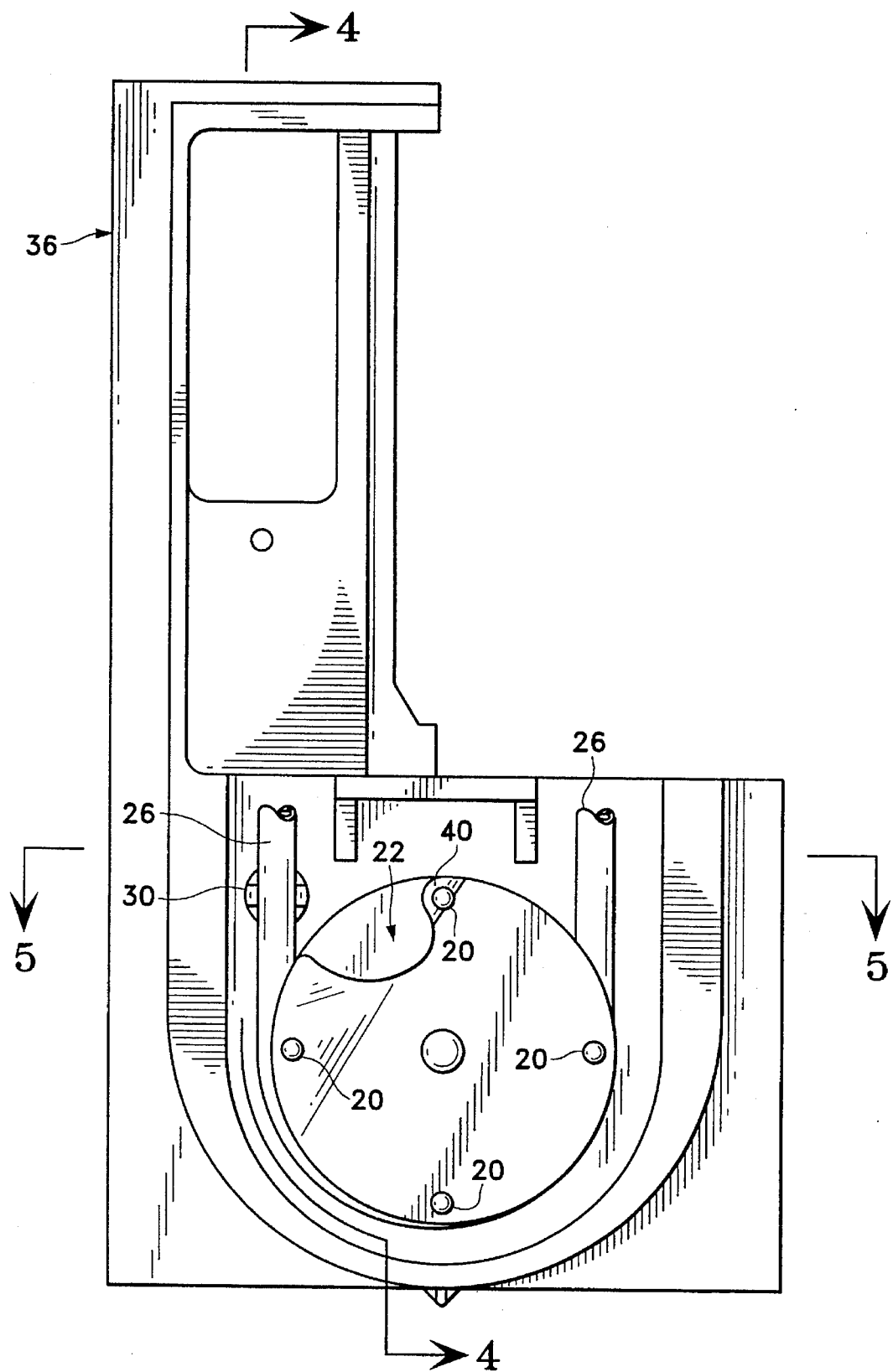
FIG. 3 is a partial elevational view of the present invention depicting the peristaltic pump tube engaged on the peristaltic pump roller head.

To disengage pump tube 26 from rollers 20, cylinder 28 is extended so that arcuate cutout 32 on tip 30 engages pump tube 26 (as seen in FIGS. 3, 4 and 5). Further extension of cylinder 28 pushes pump tube 26 away from cassette receiving portion 36 of console 38. When roller head 12 is counter-rotated, flared portion 24 and beveled portion 40 of outer plate 18 unthreads pump tube 26 from rollers 20.

This description is given for purposes of illustration and explanation. It will be apparent to those skilled in the relevant art that changes and modifications may be made to the invention described above without departing from its scope or spirit.

I claim:

1. A system for loading and unloading a surgical cassette having a peristaltic pump tube from a cassette receiving portion of a surgical console, comprising:

a) a peristaltic pump roller head having a flared and beveled notch, the roller head being located in the cassette receiving portion of the surgical console; and b) an extendable cylinder within the cassette receiving portion of the surgical console aligned so as to engage the peristaltic pump tube.

2. A surgical console, comprising:

a) a peristaltic pump roller head having a flared and beveled notch;

b) a cassette having a peristaltic pump tube stretched over the peristaltic pump roller head; and c) an extendable cylinder aligned so as to engage the peristaltic pump tube.

* * * * *